US00PP18541P2

(12) United States Plant Patent

Tupy et al.

(10) Patent No.: US PP18,541 P2
(45) Date of Patent: Mar. 4, 2008

(54) APPLE TREE NAMED 'SIRIUS'

(50) Latin Name: *Malus Mill*
Varietal Denomination: Sirius

(75) Inventors: Jaroslav Tupy, Praha (CZ); Otto Louda, Pencin u Liberce (CZ); Jan Zima, Turnov (CZ)

(73) Assignee: Institute of Experimental Botany (UEB), Praha (CZ)

( * ) Notice: Subject to any disclaimer, the term of this patent is extended or adjusted under 35 U.S.C. 154(b) by 0 days.

(21) Appl. No.: 11/522,226

(22) Filed: Sep. 15, 2006

(51) Int. Cl.
*A01H 5/00* (2006.01)

(52) U.S. Cl. ..... Plt./172

(58) Field of Classification Search ..... Plt./172
See application file for complete search history.

(56) References Cited

U.S. PATENT DOCUMENTS

PP15,963 P2 * 9/2005 Tupy et al. ..... Plt./172

OTHER PUBLICATIONS

UPOV ROM GTITM Computer Database, GTI Jouve Retrieval Software 2007/02 Citations for 'Sirius'.*

* cited by examiner

*Primary Examiner*—Wendy Haas
(74) *Attorney, Agent, or Firm*—The Webb Law Firm

(57) ABSTRACT

A new and distinct *Malus Mill.* plant that produces crisp, juicy apples having a harmonious sugar-acid balance and excellent keeping quality, suitable for use as a dessert fruit.

5 Drawing Sheets

Botanical classification: *Malus Mill.*
Varietal denomination: 'Sirius'.

BACKGROUND OF THE INVENTION

The present invention comprises a new and distinct cultivar of apple tree botanically classified as *Malus Mill.* and known by the varietal name 'Sirius'. The new variety was discovered in 1999 in The Czech Republic. The new variety is the result of a cross between 'Golden Delicious' (female parent, unpatented) and 'Topaz' (male parent, unpatented). The purpose of the breeding program was to develop late disease resistant varieties of a high fruit quality that are also suitable for organic fruit production. The new variety exhibits similar ground fruit color, the absence of fruit overcolor, and the presence of fine russet around the stem cavity to 'Golden Delicious'. Further, the new variety exhibits the trait of $V_f$-resistance against scab to 'Topaz', but exhibits triploidy, a stronger tree vigor, and very low pollen fertility compared to both parents. Further, the new variety differs from 'Golden Delicious' in its long storage capacity of fruits of common storage and the presence of $V_f$-resistance against scab. The new variety's globose to globose conical fruit form differs from the flat globose form of 'Topaz'. Further, 'Sirius' exhibits a yellow fruit color versus the yellow-red color of 'Topaz'. The following characteristics also distinguish the new variety from other *Malus Mill.* varieties known to the breeders:

- Late, dessert-type, triploid variety with good keeping quality;
- Trees exhibit strong vigor with a spreading habit;
- Low pollen fertility;
- Globose and slightly conical fruits;
- Medium to long fruit stem;
- Fine russeting around the stem cavity;

- Yellow ground color of the fruit skin, with a mostly absent overcolor;
- Flesh is firm, crispy and very juicy with a harmonic sugar/acid content and rich flavor;
- Fruits do not drop when ripe; and
- $V_f$-resistance against scab.

The new variety has been trial and field tested and has been found to retain its distinctive characteristics and remain true to type through successive asexual propagations.

DESCRIPTION OF THE DRAWINGS

The accompanying photographic drawings illustrate the new cultivar, with the color being as nearly true as is possible with color illustrations of this type. It should be noted that colors may vary with growing conditions and time of year.

DESCRIPTION OF THE PLANT

Figure 1:
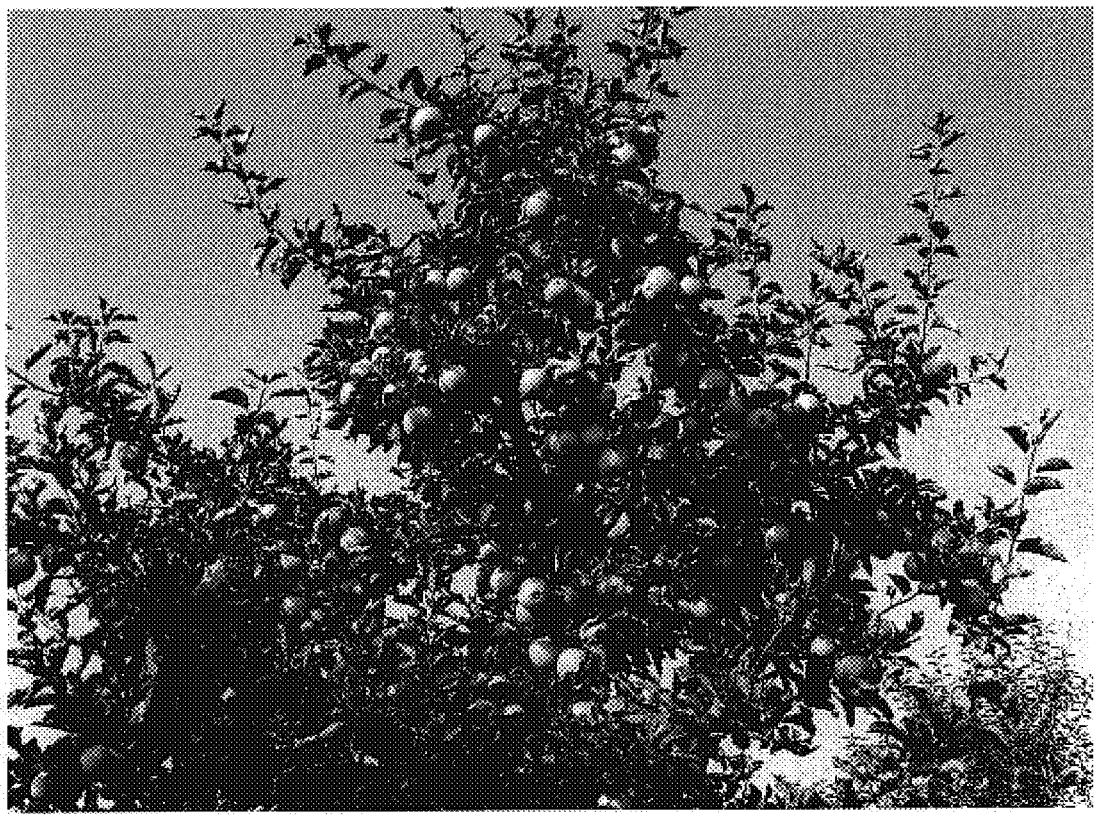
FIG. 1 is a photograph of the tree of the new variety, showing canopy form and uniformly sized fruits at maturity.
Figure 2:
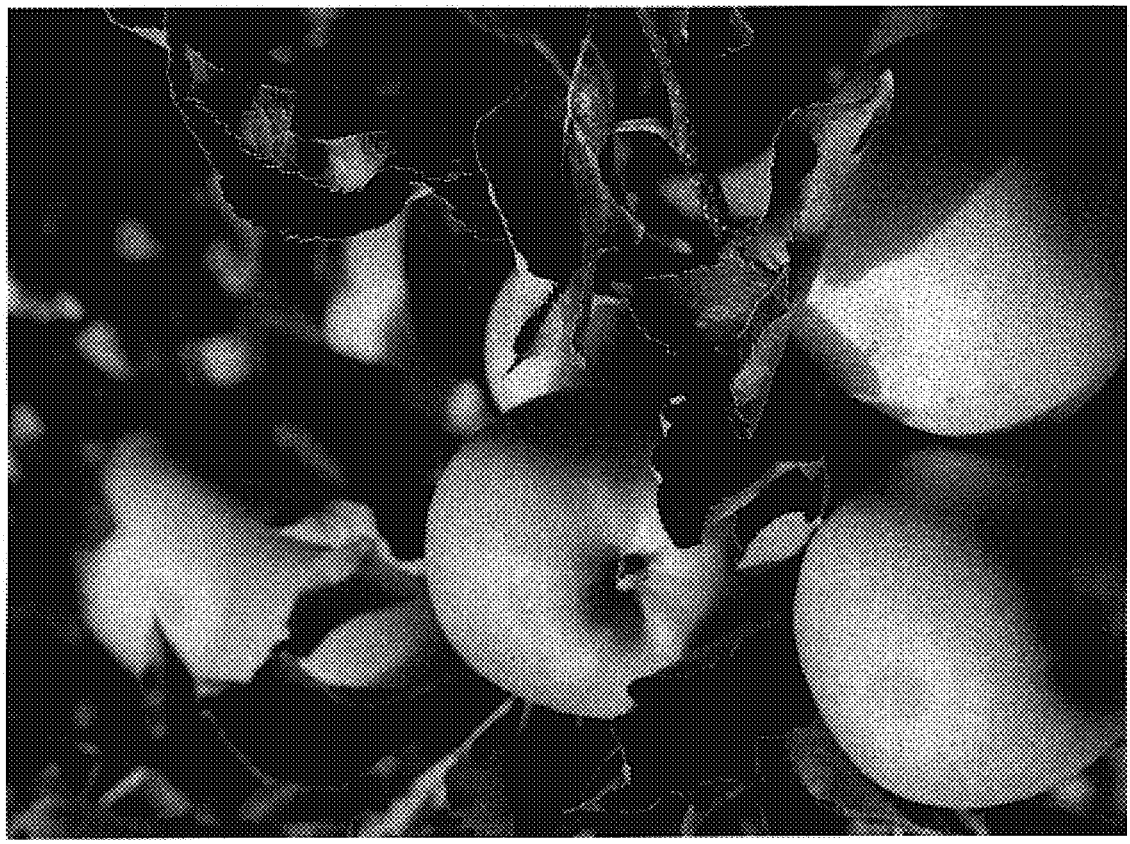
FIG. 2 shows a close-up view of the fruits of the new variety at maturity.
Figure 3:
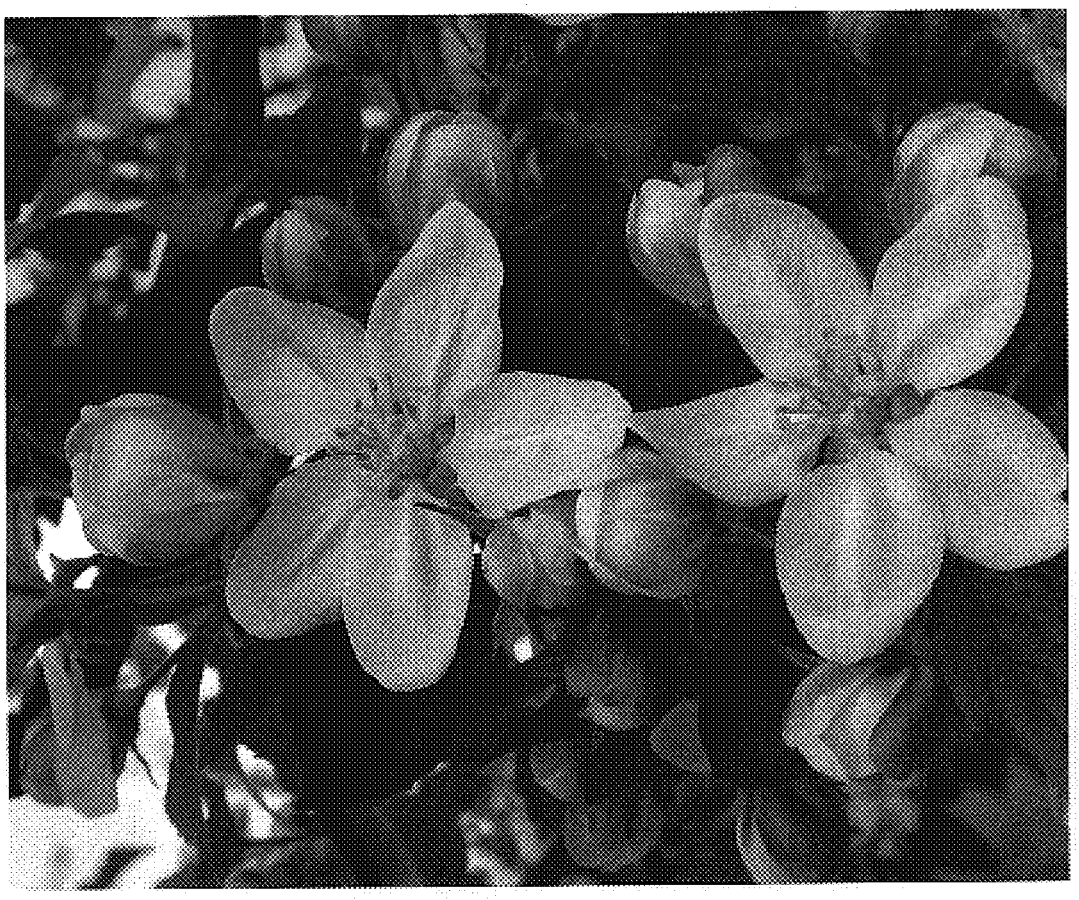
FIG. 3 shows the blossoms of the new variety.
Figure 4:
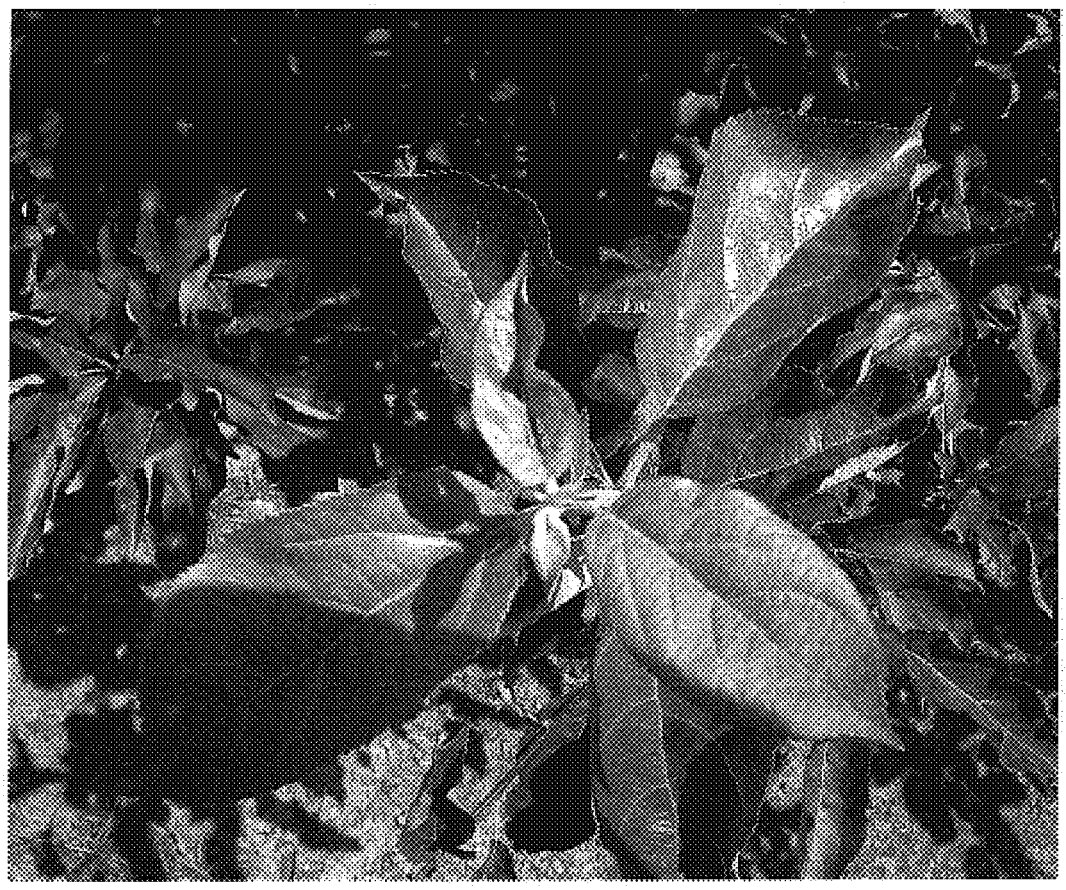
FIG. 4 shows the growing shoot of the new variety.
Figure 5:
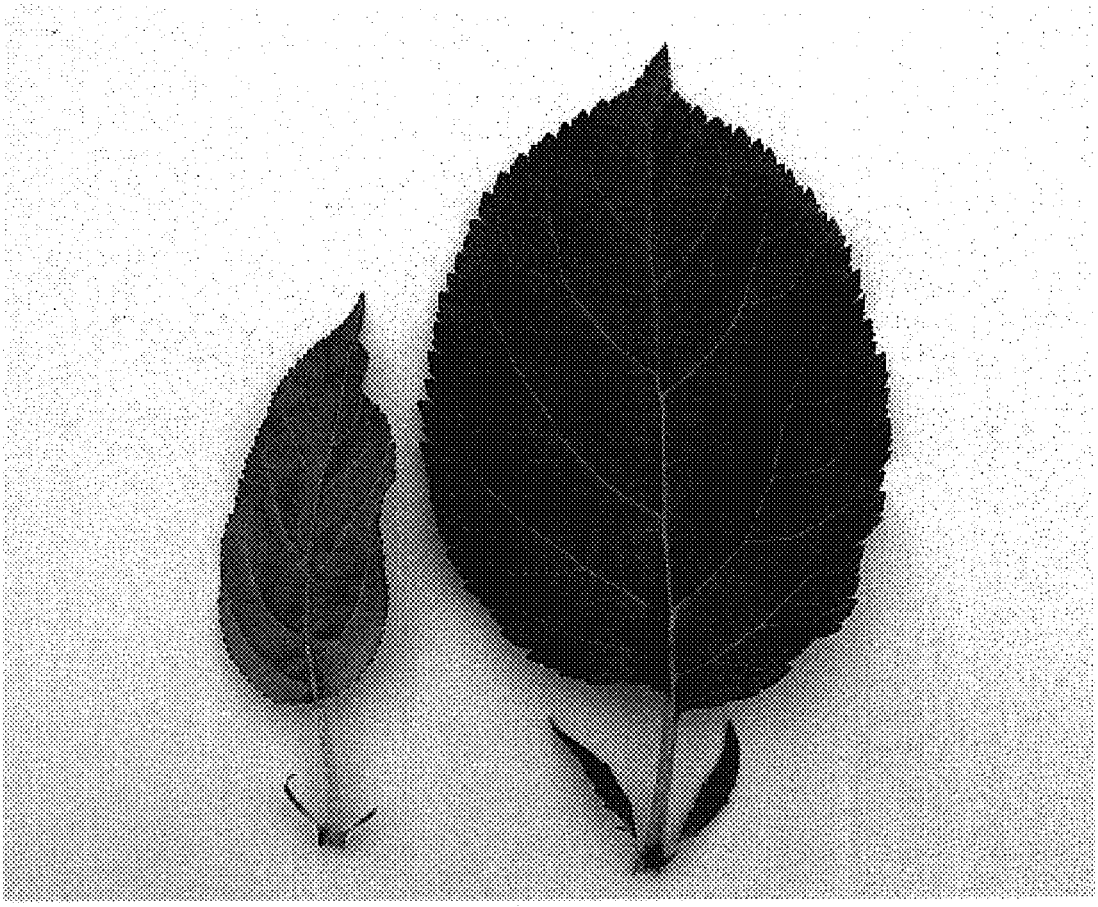
FIG. 5 shows a close-up view of the young and mature leaves of the new variety.

The following detailed description sets forth the characteristics of the new cultivar. The data which defines these characteristics was collected by asexual reproductions by budding and grafting on apple tree rootstocks first carried out in The Czech Republic. The new variety was grown under natural field conditions. The following fertilizer combination was used (Kg/ha/year): 55 parts nitrogen, 25 parts phosphorous, 60 parts potassium, 55 parts calcium, and 5 parts magnesium. Color references are primarily to the R.H.S Colour Chart of The Royal Horticultural Society of London.

TREE

Age: 14 years.
Size: 4.5 m high, 4.5 m wide.
Vigor: Strong.
Density: Open.
Form: Rounded and spreading.
Production: Moderate.
Growth Type: Ramified.
Bearing: Annual.
Trunk:
*Size.*—Approximately 17 cm in diameter at 30 cm from the soil line.
*Surface texture.*—Rough.
*Bark color.*—197A.
*Lenticels.*—(150 cm above ground):
*Length.*—1–3 mm.
*Width.*—1–1.5 mm.
*Color.*—156A to B.
*Density.*—4 lenticels per $cm^2$.
Branches:
*Diameter.*—Main branches at the trunk are 5.5 cm.
*Surface texture.*—Slightly rough, becoming rough with age.
*Color.*—One year: 200B. Two year: 200C to 201A.
*Form.*—Profuse branching.
*Average crotch angle.*—80 to 90 degrees.
*Bud arrangement.*—Alternate. Internode: 2.5 to 4.0 cm.
*Lenticels* (*on 1 year shoot*).—Length: 0.8–1.2 mm. Width: 0.8–1.0 mm. Shape: Round to oval. Density: Dense, 8 to 10 lenticels per $cm^2$. Color: 156B.
Leaves (measured at the middle of growing shoot):
*Length.*—About 90 mm to about 110 mm, averaging about 100 mm.
*Width.*—About 60 mm to about 80 mm, averaging about 70 mm.
*Form.*—Ovate to lanceolate.
*Texture.*—Smooth.
*Thickness.*—Moderately thick.
*Base.*—Predominantly symmetric.
*Apex.*—Acute.
*Margin.*—Irregularly serrate.
*Pubescence.*—Upper surface: None present. Lower surface: Very fine.
*Color.*—Young leaves: Upper surface: 146A to B. Lower surface: 147C. Mature leaves: Upper surface: 147A. Lower surface: 148B to C.
*Petiole.*—Shape: Straight to slightly bent, thickening towards the base. Length: About 20 mm to about 30 mm, averaging about 24 mm. Diameter: About 2.0 mm in the middle. Color: 144B with slight 58A at the base.
*Veins.*—Venation type: Net-like, medium dense. Color: Upper surface: 144B. Lower surface: 145B to C.
Flower buds (popcorn stage):
*Pedicel.*—Length: Typically in the range of 32–38 mm, average of 35 mm. Diameter: 1.8 mm. Color: Predominantly 144B to C with parts of 59B.
*Bud.*—Length: 16 mm. Width: 8.0 mm. Color: 64B to 64D, under the sepals the color is 65B to 65D.
Flowers:
*Bloom timing.*—2 days before 'Golden Delicious'.
*Blooming period.*—Medium.
*Pollination requirements.*—Triploid, self-sterile, needs good pollinators.
*Number of flowers per cluster.*—5.
*Fragrance.*—Faint.
*Petals.*—Number: 5. Length: From 23–25 mm, averages 24 mm. Width: From 16 to 18 mm, averages 17 mm. Shape: Ovate. Aspect: Free to overlapping. Margin: Entire. Texture and appearance: Soft and smooth. Color: When opening: Upper surface: 62D to 63D. Lower surface: 64B to C to 65D. Fully opened: Upper surface: 155C and 69B to C. Lower surface: 155D and 62B.
*Sepals.*—Shape: Long and conical with sharp points. Margin: Entire. Texture: Finely pubescent. Length: 14–15 mm from the union. Width: 3.0–4.0 mm at the middle. Color: Upper surface: 144A to 144C. Lower surface: 143C.
*Stamens.*—Number (per flower): 20. Filament length: 6–13 mm.
*Anthers.*—Shape: Oval. Length: 2 mm. Color: 10A.
*Pollen.*—Color: 11A. Amount (generally): Medium.
*Pistils.*—Length: 17 mm.
*Style.*—Length: 13 mm. Color: 144B.
*Stigma.*—Shape: Rounded. Color: 153B to C.
Fruit:
*Maturity when described.*—Eating maturity — after 2 months in common storage.
*Date of picking.*—Oct. 24, 2005.
*Size.*—Axial diameter: Average 74.5 mm. Transverse diameter: Average 80.9 mm.
*Form.*—Globose to globose conical, symmetrical with a length:width ratio of 0.9.
*Cavity.*—Shape: Acuminate. Depth: Typically between 11–15 mm. Breadth: Typically between 29–34 mm.
*Basin.*—Shape: Wide, smooth, slightly ribbed. Depth: Typically between 6–9 mm. Width: Typically between 28–32 mm.
*Calyx.*—Persistent and open.
Skin:
*Thickness.*—Medium.
*Texture.*—Smooth.
*Tendency to crack.*—Absent.
*Color.*—Overcolor absent or occasionally as a low 24B blush.
*Ground color.*—13A.
Flesh:
*Aroma.*—Medium.
*Color.*—15D.
*Texture.*—Firm, crisp, fine grained, juicy.
*Eating quality.*—Very good, rich flavor, well-balanced sugar (14–15% Brix) and acid level.
Core:
*Bundle area.*—On longitudinal section defined with vascular strands, width 26 mm, length 28 mm, core locules open.
*Bundle.*—Vascular strands medium distinct.
*Calyx tube.*—Cylindrical and short.
*Styles.*—Dry remnants present.
*Stamens.*—Dry remnants present.
*Seed cells.*—Wall: Smooth. Depth: About 8 mm. Breadth: About 3 mm. Longitudinal section: About 20 mm (length of seed cell).
Seeds:
*Number perfect.*—2 to 3.
*Number in one cell.*—0 to 1.

*Length.*—About 9 mm.
*Breadth.*—About 4 mm.
*Form.*—The tip is acute to obtuse, can be flattened.
*Color.*—166A.

Stem:
*Length.*—Typically between 23–38 mm, average of 30 mm.
*Width.*—About 2 mm.
*Color.*—Brownish.

Use: Late very good dessert variety suitable for both conventional and organic growing as well as for home gardens.

Shipping quality: Very good.

Keeping quality: Very good, at least 6 months in common storage.

Tree winter hardiness: No frost damage observed at the place of origin, lowest winter temperatures approximately −20° C.

Bud winter hardiness: No frost damage observed at the place of origin, lowest winter temperatures approximately −20° C.

Drought tolerance: Unknown.

Disease resistance: $V_f$-resistance against scab.

I claim:

1. A new and distinct variety of *Malus Mill* plant substantially as is herein described and illustrated.

* * * * *